(12) United States Patent
Morazzoni et al.

(10) Patent No.: US 9,556,099 B2
(45) Date of Patent: Jan. 31, 2017

(54) HYPERFORIN DERIVATIVES AND THEIR USE IN ALZHEIMER'S DISEASE

(71) Applicant: INDENA S.P.A., Milan (IT)

(72) Inventors: Paolo Morazzoni, Milan (IT); Antonella Riva, Milan (IT); Gabriele Fontana, Milan (IT)

(73) Assignee: INDENA S.P.A., Milan (IT)

(*) Notice: Subject to any disclaimer, the term of this patent is extended or adjusted under 35 U.S.C. 154(b) by 0 days.

(21) Appl. No.: 14/892,153

(22) PCT Filed: Jun. 17, 2014

(86) PCT No.: PCT/EP2014/062707
§ 371 (c)(1),
(2) Date: Nov. 18, 2015

(87) PCT Pub. No.: WO2014/202597
PCT Pub. Date: Dec. 24, 2014

(65) Prior Publication Data
US 2016/0115111 A1    Apr. 28, 2016

(30) Foreign Application Priority Data
Jun. 19, 2013 (IT) .................. MI2013A1012

(51) Int. Cl.
*C07C 49/757* (2006.01)
*C07C 45/67* (2006.01)

(52) U.S. Cl.
CPC ........... *C07C 49/757* (2013.01); *C07C 45/673* (2013.01); *C07C 2102/46* (2013.01)

(58) Field of Classification Search
None
See application file for complete search history.

(56) References Cited

FOREIGN PATENT DOCUMENTS

WO    03091194 A1    11/2003

OTHER PUBLICATIONS

International Search Report and Written Opinion of PCT/EP2014/062707 of Oct. 27, 2014.

*Primary Examiner* — Alicia L Otton
(74) *Attorney, Agent, or Firm* — Silva Salvadori, P.C.; Silvia Salvadori

(57) ABSTRACT

Disclosed is a compound having the formula a) or b); a: $R=CH_3$; b: $R=CH_2CH_3$, and its use in the prevention and/or treatment of Alzheimer's disease.

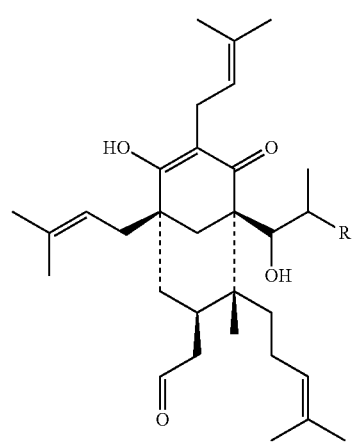

(I)

4 Claims, No Drawings

HYPERFORIN DERIVATIVES AND THEIR USE IN ALZHEIMER'S DISEASE

This application is a U.S. national stage of PCT/EP2014/062707 filed on 17 Jun. 2014, which claims priority to and the benefit of Italian Application No. MI2013A001012 filed on 19 Jun. 2013, the contents of which are incorporated herein by reference in their entireties.

FIELD OF INVENTION

The present invention relates to hyperforin derivatives, their use in the pharmaceutical and/or nutritional field, in particular for the prevention and treatment of Alzheimer's disease, and pharmaceutical formulations containing said derivatives.

TECHNICAL BACKGROUND

The flowering tops of *Hypericum perforatum* (St John's wort) contain a large number of structurally different substances which act directly or indirectly on the central nervous system. Among said substances, hyperforin, a phloroglucinol derivative, is one of the main constituents, together with adhyperforin, of the lipophilic fraction obtained from the flowering tops of the plant (Erdelmeier C. A. J., Pharmacopsychiatry 31, 2, 1998).

Hyperforin has formed the subject of numerous studies, which have demonstrated a potent antidepressant activity (Laakman G. et al., Pharmacopsychiatry 31, 54, 1998; Butterweck V. et al., Life Science 73, 627, 2003).

Moreover, salts with inorganic or ammonium cations of hyperforin and adhyperforin have been described as having an important action for the prophylaxis and treatment of Alzheimer's disease (WO99/41220).

It is also known from the literature that hyperforin is highly unstable under the usual extraction and storage conditions, and derivatives have been devised to improve its stability (WO99/41220, WO99/64388).

In particular, more stable hyperforin and adhyperforin derivatives have been developed by total reduction of the double bonds of the isoprene chains and reduction to hydroxyl groups of the keto groups in the 1 and 10 positions (Bystrov N. S. et al., Bioorg. Khim. 4, 791, 1978). These derivatives have proved not only more stable, but also much more effective as antidepressants, anxiolytics and anti-neurodegenerative drugs (WO03/091194).

It has now surprisingly been found that the hyperforin and adhyperforin derivatives obtainable by reduction to hydroxy groups of the ketones in the 1 and 10 position described in WO03/091194 can in turn, by hydroxylation followed by deisopropylation, give rise to novel products which cross the blood-brain barrier more efficiently and inhibit neuropathological damage induced by Aβ fibrils in different experimental models.

DESCRIPTION OF THE INVENTION

The present invention relates to the following hyperforin and adhyperforin derivatives of formula a) and b) respectively:

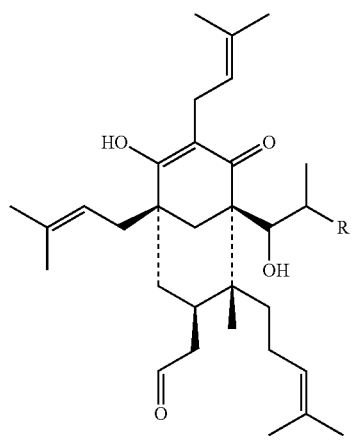

a: R = CH$_3$
b: R = CH$_2$CH$_3$

Compound a) is deisopropyl-dehydro tetrahydro hyperforin.

Compound b) is deisopropyl-dehydro tetrahydro adhyperforin.

The two compounds can be used in the medical and/or nutritional field, in particular for the treatment of Alzheimer's disease. The products according to the invention have proved able to penetrate the blood-brain barrier, and are particularly effective in inhibiting neuropathological damage, such as that which develops in Alzheimer's disease.

The subject of the present invention is therefore the use of said compounds in the prevention and treatment of Alzheimer's disease.

A further subject of the present invention is pharmaceutical formulations containing the compounds of formulas a) and b). Said formulations can, for example, take the form of soft gelatin capsules, hard gelatin capsules, tablets, suppositories and controlled-release formulations, prepared by known methods such as those reported in Remington's Pharmaceutical Sciences Handbook, 17th ed., Mack Pub., NY, USA.

The preferred pharmaceutical formulations are soft or hard gelatin capsules, tablets and transdermal patches.

In the latter case, controlled-release compounds can be administered by applying the patch in the area proximal to the arterial branches of the cerebral carotids.

The dose of the compounds in the formulations can range between 10 and 100 mg/dose/day.

Example 1

Determination of the Plasma and Brain Levels of Hyperforin and the Derivatives According to the Invention in Mice Treated Subacutely by Intraperitoneal Administration In mice treated subacutely (twice a day for 4 days) by intraperitoneal administration at the dose of 20 mg/kg of the products according to the invention, their brain and plasma levels were determined by a combined HPLC/MS/MS analysis technique developed on the basis of a method already described by Keller J. H. et al. (Anal. Chem. 75, 6084, 2003).

The results set out in Table 1 below demonstrate the presence of the products according to the invention in the brain. The levels observed exceed those measured after administration of an equal dose of hyperforin, this finding being in line with those reported in the literature (Keller J. H. et al., Anal. Chem. 75, 6084, 2003; Rozio M. et al., J. Chromatogr. B. 816, 21, 2005).

TABLE 1

Plasma and brain levels of hyperforin and the derivatives according to the invention in mice treated subacutely (twice a day for 4 days) by intraperitoneal administration with 20 mg/kg

| Product | Time (h) | Plasma (ng/ml) | Brain (ng/g) | Brain/Plasma % |
|---|---|---|---|---|
| Hyperforin | 0 | 624.5 ± 81.8 | 15.2 ± 16.1 | 1.89 ± 0.91 |
|  | 1 | 1547.2 ± 226.6 | 21.1 ± 7.4 | 1.24 ± 0.75 |
|  | 2 | 1421.3 ± 235.4 | 23.2 ± 7.8 | 1.32 ± 0.82 |
|  | 4 | 1275.4 ± 212.8 | 32.3 ± 8.1 | 1.91 ± 0.91 |
|  | 6 | 1192.6 ± 196.5 | 35.6 ± 8.8 | 2.12 ± 1.12 |
| Deisopropyl-dehydro tetrahydro hyperforin (a) | 0 | 1339.5 ± 283.8 | 62.1 ± 34.6 | 3.89 ± 1.33 |
|  | 1 | 4270.0 ± 1237.8 | 78.5 ± 16.2 | 2.76 ± 1.62 |
|  | 2 | 2947.8 ± 961.6 | 63.1 ± 9.8 | 2.93 ± 0.95 |
|  | 4 | 2870.0 ± 426.2 | 256.6 ± 112.4 | 12.24 ± 7.64 |
|  | 6 | 2235.0 ± 264.8 | 367.3 ± 76.6 | 17.04 ± 1.37 |
| Deisopropyl-dehydro tetrahydro adhyperforin (b) | 0 | 1262.4 ± 272.3 | 59.1 ± 28.5 | 3.78 ± 1.25 |
|  | 1 | 3971.2 ± 984.5 | 61.4 ± 19.6 | 1.51 ± 0.96 |
|  | 2 | 2756.4 ± 622.3 | 60.2 ± 21.4 | 2.05 ± 1.71 |
|  | 4 | 2564.1 ± 531.4 | 195.6 ± 60.6 | 6.51 ± 3.25 |
|  | 6 | 2120.4 ± 410.6 | 251.8 ± 71.2 | 10.56 ± 6.25 |

Each value is the mean±S.E. of 4 animals. Time 0 corresponds to the 14th hour after the previous treatment Example 2

Effect of Hyperforin and the Derivatives According to the Invention on Neuropathological Damage Induced by Aβ In Vivo The products according to the invention have proved to be particularly effective in inhibiting neuropathological damage induced by Aβ fibrils in vivo. To evaluate the potential neuroprotective effect of the products according to the invention, male rats were treated stereotactically in the dorsal hippocampus with 80 μg of Aβ fibrils in the presence or absence of the products. The injection of Aβ fibrils produces proliferation and an increase in astrocyte density, an increase in the soma and GFAP staining in the astrocytes present around the injection site.

The results set out in Table 2 below demonstrate that co-administration of the products according to the invention with Aβ fibrils significantly reduces astrocyte proliferation (compared with the group treated with Aβ fibrils alone), reduces GFAP staining and completely abolishes enlargement of the astrocytic perikaryon.

TABLE 2

The effect of hyperforin and the derivatives according to the invention on neuropathological damage induced by Aβ in vivo

| Product | Density of reactive astrocytes (GFAP+ cell./4 × $10^3$ μm$^2$) | GFP intensity of the astrocyte soma (arbitrary unit) | Measurement of astrocyte soma (arbitrary unit) | Number of neurones in the dentate gyrus (cell./ 4 × $10^3$ mm$^2$) |
|---|---|---|---|---|
| Control | 11 ± 4 | 134 ± 11 | 101 ± 18 | 119 ± 19 |
| Aβ (fibrils only) | 39 ± 7 | 259 ± 9 | 310 ± 16 | 58 ± 7 |
| Hyperforin (+fibrils) | 37 ± 6 | 248 ± 7 | 306 ± 14 | 62 ± 8 |
| Deisopropyl-dehydro tetrahydro hyperforin (+fibrils) | 22 ± 3* | 150 ± 19* | 105 ± 8* | 161 ± 14** |
| Deisopropyl-dehydro tetrahydro adhyperforin (+fibrils) | 24 ± 4 | 165 ± 17* | 117 ± 9* | 121 ± 11* |

The β-amyloid fibrils were injected stereotactically into the hippocampus, either alone or in combination with hyperforin and the derivatives according to the invention.
*p < 0.05; **p < 0.001 [vs Aβ (fibrils only)].

The invention claimed is:
1. A compound having the following formula a) or b):

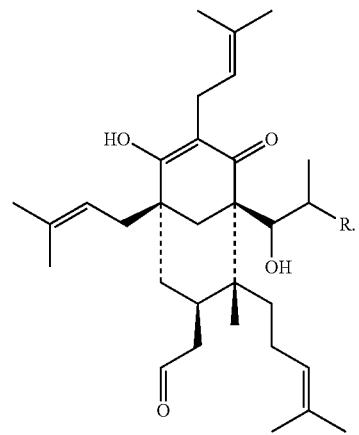

a: R = CH$_3$
b: R = CH$_2$CH$_3$

2. A medicament comprising the compound according to claim 1.
3. A pharmaceutical composition containing the compound of formula a) or b) as claimed in claim 1 and a pharmaceutically acceptable excipient and/or carrier.
4. A method of treating Alzheimer's disease in patients in need thereof, said method comprising administering an effective amount of the medicament according to claim 2 to said patients.

* * * * *